United States Patent [19]

Sibalis

[11] Patent Number: 5,135,478
[45] Date of Patent: Aug. 4, 1992

[54] MULTI-SIGNAL ELECTRICAL TRANSDERMAL DRUG APPLICATOR

[75] Inventor: Dan Sibalis, Stony Brook, N.Y.

[73] Assignee: Drug Delivery Systems Inc., New York, N.Y.

[21] Appl. No.: 349,996

[22] Filed: May 10, 1989

[51] Int. Cl.⁵ .............................................. A61N 1/30
[52] U.S. Cl. ..................................................... 604/20
[58] Field of Search ................ 604/20, 21; 128/803, 128/419 R, 420 R, 421

[56] References Cited

U.S. PATENT DOCUMENTS

| | | | |
|---|---|---|---|
| 3,924,641 | 12/1975 | Weiss | 128/421 X |
| 4,702,732 | 10/1987 | Powers et al. | 604/20 |
| 4,764,164 | 8/1988 | Sasaki | 604/20 |
| 4,786,278 | 11/1988 | Masaki | 604/20 |
| 5,042,975 | 8/1991 | Chien et al. | 604/20 |

FOREIGN PATENT DOCUMENTS

| | | | |
|---|---|---|---|
| 2502015 | 9/1982 | France | 604/20 |
| 2041752 | 9/1980 | United Kingdom | 604/20 |
| 2132892 | 7/1984 | United Kingdom | 604/20 |

*Primary Examiner*—Lee S. Cohen
*Attorney, Agent, or Firm*—Lackenbach Siegel Marzullo & Aronson

[57] ABSTRACT

A transdermal application for attachment to the skin having at least one drug reservoir containing at least one drug, and having an electrical connection formed at a surface interface between said reservoir upon contact with said skin; means for causing said at least one drug to move through said interface transdermally and for maintaining said transdermal movement for an extended time period. The means for causing and maintaining transdermal movement including a source of varying electrical potential, said source having one terminal electrically connected to said at least one reservoir at a location away from said skin surface interface and an other terminal in circuit with said skin surface at a location away from said reservoir/skin surface interface. The electrical circuit is formed upon application to the skin of the device, and said circuit connecting from said one source terminal through said at least one reservoir, through said reservoir/skin surface interface, within said skin to said skin surface connected in circuit to said other source terminal, wherein the drug is delivered through said skin when electrical current flows in a first direction in the circuit. The varying electrical potential is the resultant combination by at least one of superposition and selection of a plurality of electrical signals, and the electrical source including at least one of means for storing data representative of said resultant and means for generating the plurality of signals, and means for selecting and superposing the signals in selected time relationships for application to the source terminals.

5 Claims, 4 Drawing Sheets

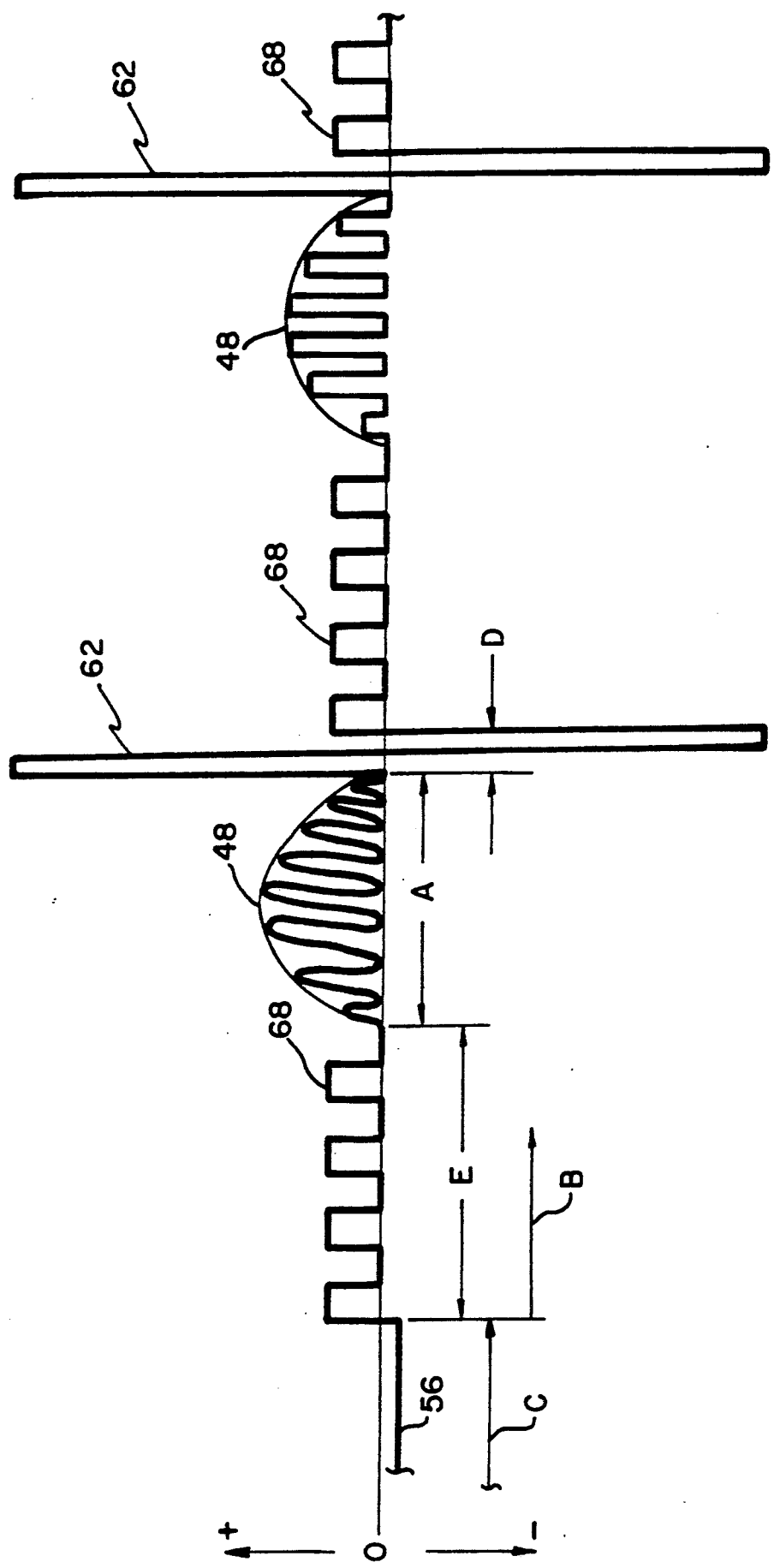

MULTI-SIGNAL ELECTRICAL TRANSDERMAL DRUG APPLICATOR

BACKGROUND OF THE INVENTION

This invention relates generally to an electrical transdermal drug device delivering a drug to the patient for systemic distribution by blood flow using principles of electrokinetic phenomena, such as electrophoresis and electroosmosis, and more particularly to an electrical transdermal drug applicator using a plurality of interposed and superposed signals of varying electrical potential which extend the period of therapeutic drug delivery and thereby increase usefulness of the drug applicator. Reference to or disclosure of devices for transdermal delivery of drugs by application of electrical current through the skin of a person or animal are shown in the following U.S. Pat. Nos.:

| | |
|---|---|
| 385,556 | 4,243,052 |
| 486,902 | 4,325,367 |
| 588,479 | 4,367,745 |
| 2,493,155 | 4,419,019 |
| 2,267,162 | 4,474,570 |
| 2,784,715 | 4,406,658 |
| 3,163,166 | 4,314,554 |
| 3,289,671 | 4,166,457 |
| 3,547,107 | 4,239,052 |
| 3,677,268 | 4,290,878 |
| 4,008,721 | 4,164,226 |
| 4,141,359 | 4,362,645 |
| 4,239,046 | 4,273,135 |

The following foreign patents refer to disclosed transdermal drug delivery devices:
EPA No. 0060452
DE No. 290202183
DE No. 3225748
EPA No. 0058920
UK NO. 2104388

Thus, it is evident, that transdermal delivery of drugs by application of an electrical current is not unknown. Yet, except for experimental and developmental purposes, such electrical transdermal drug applicators are not presently commercially available for use by medical professionals or by individuals.

A problem with transdermal patches, especially electronically powered patches, is that such devices exhibit a rate of drug delivery which decays with passage of time despite a steady state condition for the applied electrical current and steady state drug concentrations within the drug reservoir of the device. This phenomenon has been reported in scientific journals, for example, an article, IN VIVO TRANSDERMAL DELIVERY OF INSULIN, Chien et al, Annals of New York Academy of Sciences, pages 38–47 (1987).

Therein, changes in blood glucose level are recorded versus time after insulin is delivered transdermally to laboratory animals using an electrical current. Several parameters are varied. For example, it is reported that a pulsed DC current has a greater and more enduring effect in reducing blood glucose levels in laboratory animals than does a pure continuous DC current. The actual quantity of insulin which is delivered is not measured. Rather the effect of the drug in reducing blood glucose levels is measured. It is found that one repetition rate of DC pulses is more effective than another pulse repetition rate in reducing blood glucose levels measured both in magnitude of reduction and time duration. A square waveform provided better results than did a sinusoidal waveform or a trapezoidal waveform.

The authors of the paper analogize the skin electrically with resistances and capacitances in parallel as an equivalent circuit. They theorize that the DC current polarizes the skin, that is, charges the capacitance of the skin which, once charged, can accept no more current and accordingly limits drug delivery. Using DC pulses rather than steady state current allows time for the skin capacitance to discharge, such that on the next pulse, additional current, capacitor charging, and drug delivery can occur.

However, an anomalous situation arises when at a favorable pulse repetition rate, and with the same current delivery level as in prior tests, the duty cycle is varied. It would be expected that the greater the duty cycle, that is, the greater the current ON time versus the current OFF time ratio, the greater amount of insulin would be delivered transdermally and the measured effects on blood glucose level would be correspondingly more favorable and more enduring. Contrary to expectations, as the duty cycle increases from a one to one ratio toward an eight to one ratio, the reduction in blood glucose level becomes less, rather than more, although duration of this glucose level reduction is somewhat extended.

In summary, application of electrical current over a longer period of time, that is, delivering more electrical energy transdermally for delivering drugs, results in what appears to be continuously decreasing delivery of drug.

That publication graphically illustrates the problem with prior art transdermal drug applicators and delivery methods using electrical current to carry drugs through the skin, that is, the effectiveness of the delivered drug is insufficient in duration and therapeutic effect and the rate of drug delivery falls off as the delivering current is continuously applied over extended periods of time.

What is needed is a transdermal drug applicator which provides enhanced drug delivery to the patient with regard to quantity of systemically delivered drug and duration of drug effectiveness.

SUMMARY OF THE INVENTION

Generally speaking, in accordance with the invention, an electrical transdermal drug applicator having enhanced drug flow to the bloodstream of the subject is provided.

A plurality of electrical signals of varying potential is applied across the skin which is in circuit with a drug reservoir in the applicator. Each signal is selected in duration, repetition rate, shape and harmonic content to maintain or enhance local blood circulation by dilating the blood vessels proximate the patch and by impeding the process of blood coagulation and vasoconstriction associated with the passage of electrical current through the skin. In some instances, electrical signals are superposed on other signals, whereas independent application of each signal is also considered favorable with all signals being contained within an overriding repetition rate format.

A voltage source and suitable signal generating and timing circuits are provided in a self-contained transdermal applicator.

The multi-signal techniques may be applied in the more conventional transdermal drug applicators as listed above and in more complex devices, which may include counteractors, as set forth in commonly assigned, co-pending U.S. patent application, entitled Electrical Transdermal Drug Applicator With Counteractor And Method Of Drug Delivery, Ser. No. 287,348, filed Dec. 21, 1988, now U.S. Pat. No. 5,088,977.

Accordingly, it is an object of the invention to provide an improved electrical transdermal drug applicator which provides enhancement of drug flow into the circulatory system of the subject by applying selected AC and DC wave forms, of selected frequencies, shapes, durations, repetition rate, etc.

Another object of the invention is provide an improved electrical transdermal drug applicator which uses electrical signals to cause the body to manufacture its own vasodilators and thrombolytic compounds.

Yet another object of the invention is to provide an improved electrical transdermal drug applicator which applies electrical signals to increase the fibrinogen clotting time in the patient.

Still another object of the invention is to provide an improved electrical transdermal drug applicator for applying electrical signals to improve drug delivery from solutions.

Still another object of the invention is to provide an improved electrical transdermal drug applicator which applies signals to improve drug delivery from gels.

Still another object of the invention is to provide an improved electrical transdermal drug applicator to improve drug delivery from oils.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 2a is a wave form of a composite signal produced by the electrical transdermal drug applicator of FIG. 1; and FIG. 2b is an enlarged portion of FIG. 2a;

DESCRIPTION OF THE PREFERRED EMBODIMENTS

Figure 1:
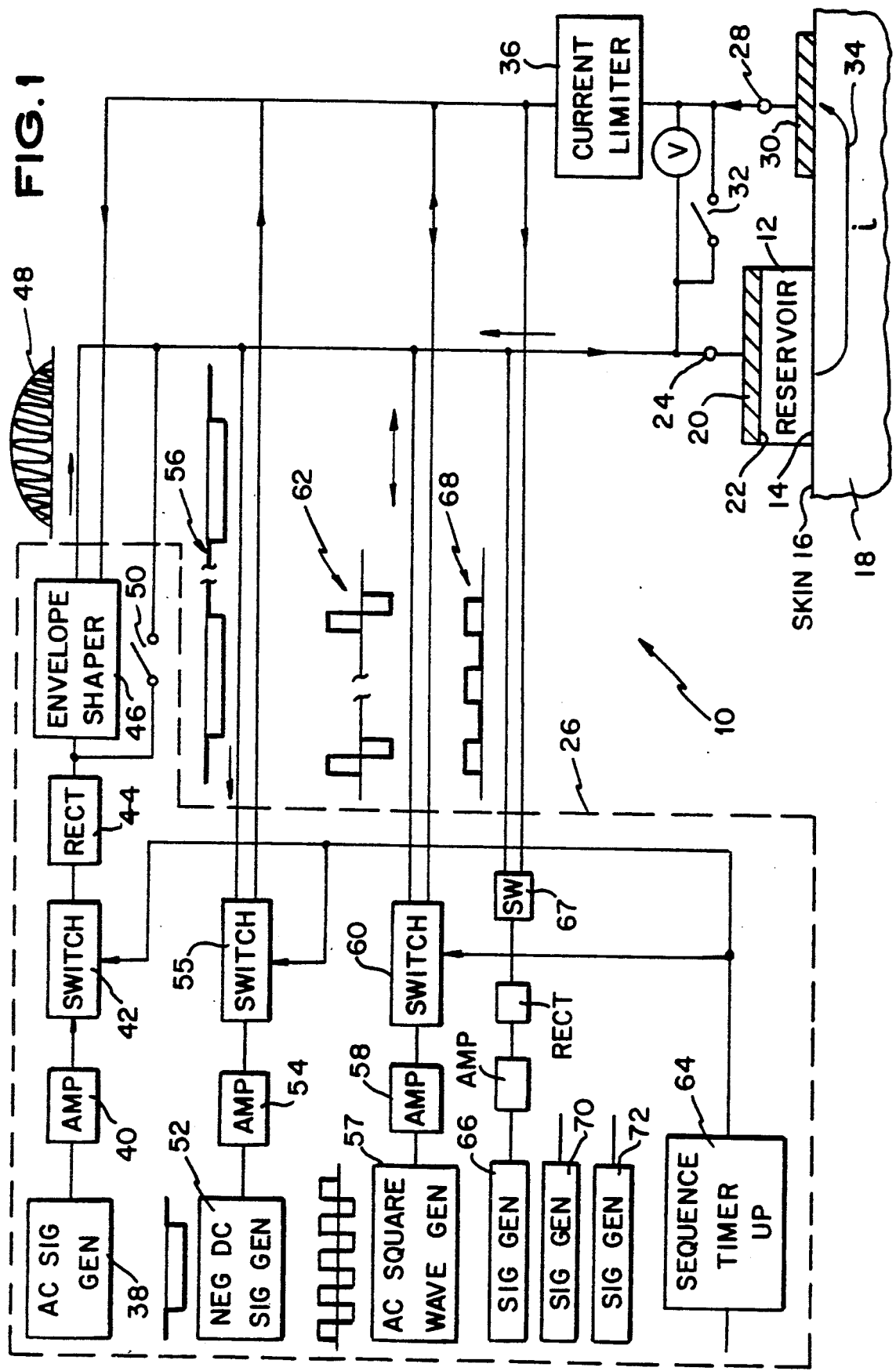
FIG. 1 is a schematic diagram of a multi-signal electrical transdermal drug delivery applicator in accordance with the invention.

With reference to FIG. 1, a multi-signal electrical transdermal drug applicator 10 in accordance with the invention includes a reservoir 12 containing a drug dispersed in a suspension, for example, a gel as disclosed in any of the above-referenced patents by the inventor here, as examples. A surface 14 of the reservoir 12 rests against the surface 16 of the user's skin 18 and is maintained in position, for example, by an adhesive (not shown). An electrode 20 connects to another surface 22 of the reservoir 12 and the electrode 20 connects to an external terminal 24 of a signal generating and timing unit 26. The other external terminal 28 of the signal generating and timing unit connects to the skin surface 16 by way of a return electrode 30 which contacts the skin and is maintained in position, for example, by an adhesive (not shown). A single pole switch 32 is connected between the external terminals 24, 28. The gel and drug are contained in the reservoir 12 in a manner to prevent leakage of the substances. Also, there is no short circuit of electrical current across the skin surface 16 directly from the reservoir 12 to the electrode 30.

It is well established that what when a voltage difference of proper magnitude and polarity, is applied across the external terminals 24, 28, drug from the reservoir 12 enters the body of the user through the skin surface 16 while a current flows through the skin 18 as indicated by the arrow 34. The current 34 is algebraically indicated and includes currents flowing in the opposite direction. For example, a positive potential on the electrode 20 relative to the skin and electrode 30 produces a current in the direction illustrated, whereas a negative potential on electrode 20 relative to the skin and electrode 30 will produce a current through the skin 18 in the opposite direction (not illustrated).

In the illustrated embodiment of FIG. 1, the current circuit includes a current limiter 36 which restricts the upper value of current which can flow through the skin 18, therefore avoiding the hazards of burns and possible skin irritation of the skin where the electrodes make contact.

The signal generating and timing unit 26 includes a plurality of signal generating circuits. Therein, an AC signal generator 38 outputs an AC pulse at a carrier frequency which passes through a buffer amplifier 40, a closed switch 42, and is rectified to DC by a rectifier 44. The rectified signal is passed through a shaping circuit 46, wherein a half-sine waveshape envelope is applied, providing a positive output pulse 48 as indicated. Signal amplification may not be necessary.

The detailed constructions of the circuits in the schematic representations herein are believed to be state-of-the-art and present no obstacle to implementation by those skilled in the art.

A by-pass, schematically represented by switch 50, allows the rectified signal to go directly to the external terminal 24, thus providing a rectangularly shaped positive pulse rather than a half-sine wave pulse. The AC carrier frequency within the pulse 48 is 2500 Hz plus or minus 1000 Hz. The original AC signal from the generator 38 may be a sine or square wave. The pulse 48 has a width of 6.25 ms plus or minus 5 ms, for example, that is the sine wave shape has a nominal duration corresponding to the period of a frequency of 160 Hz, and a repetition rate of 80 pulses per second $\pm 20$ pulses per second. This repeating signal continues for an interval B, for example, one minute $\pm 20$ seconds and then is off for an interval C, for example, one minute, after which it is on for an interval B, and so on. After minutes of operation, for example thirty minutes for delivery of insulin, the switch 50 is closed such that rectangular pulses replace the half-sine wave pulse indicated at 48. A two minute period (B+C) corresponds to a frequency of 0.008 Hz. Ramped and trapezoidal pulse envelopes may be used and particular drugs may benefit in delivery by other envelope shapes.

It should be understood that all frequencies, pulse widths, repetition rates, amplitudes, etc. used in describing performance herein are nominal and are intended to include a range of values even when the range is not immediately defined.

A parallel signal generator 52 outputs a negative DC signal which passes through a buffer amplifier 54, a switch 55, and is applied to the electrode 20. When the switch 55 is closed, a negative voltage of 0.8 volts ±0.4 volts is applied at the electrode 20. This causes a current to flow through the skin 18 in a direction opposite to that indicated by the arrow 34. The negative voltage is applied during the C interval when the shaped pulse 48 (and other signals described hereinafter) is not applied.

A parallel AC square wave generator 57 outputs a square wave AC signal to an amplifier 58, then to a switch 60, and the signal is applied to the electrode 20. The period D of the square wave is, for example, 0.4 ms plus or minus 0.2 ms, corresponding to a frequency of 250 Hz. The switch 60 is operated to pass a single AC cycle at a repetition rate of 80 cycles per second during the interval D as indicated at 62.

A second parallel AC square wave generator 66 is similar to the wave generator 57. The output of the generator 66 is amplified, rectified, passes through a switch 67, and also is applied to the terminal 20. The signal output 68 has a frequency of approximately 770 Hz plus 100 Hz, minus 200 Hz and is output for a period E, for example, of 4 ms plus or minus 2 ms during the interval B.

Figure 2B:
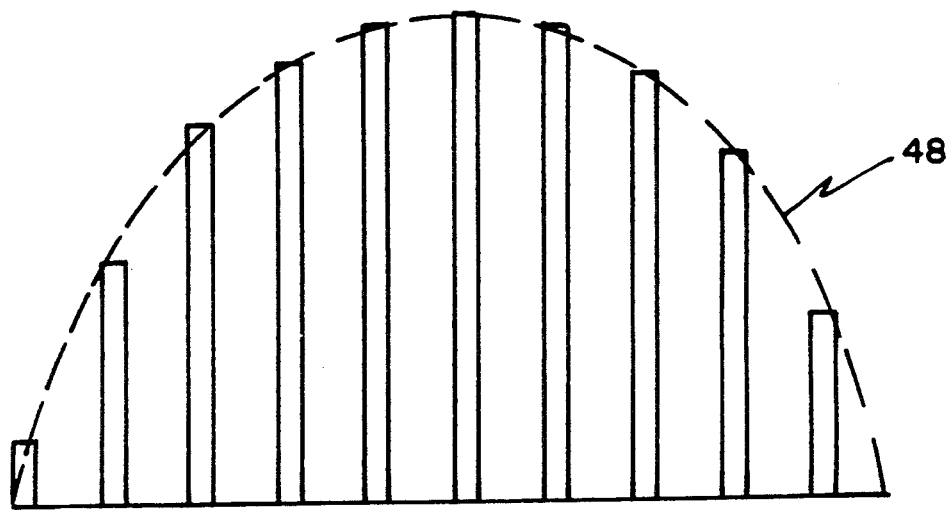

A sequence timer 64 including a microprocessor controls the switches 42, 55, 60, 67 to produce the total wave form signal with desired timing in a desired sequence of signal components. FIG. 2a illustrates an exemplary sequence and timing of signals wherein the initial signal is the negative 0.8 volt signal 56 followed by the rectified 770 Hz square wave signal 68, which is in turn followed by a pulse 48. The pulse 48 is followed by a single AC cycle, the signal 62. In an embodiment in accordance with the invention, the negative signal 56 is applied for one minute. The signals 68, 56, 62 occur within one-eightieth second, that is, 12.5 ms, and are repeated for one minute (4800 repetitions) after which the signal 56 of minus 0.8 volts is applied again for one minute. It is preferred that the applicator 10 always start-up with the negative DC signal 56. The first pulse 56 may be of duration greater or less than the nominal one minute used thereafter.

Additional signal generators 70, 72 are illustrated (FIG. 1) to indicate that the number of signals which may be applied across the electrodes 20, 30 is not limited. When closed, the switch 32 provides a short circuit between the electrodes 20, 30, such that charges, if any, built up within the skin 18 during the driving periods may be used to produce current flow within the blood capillaries which is of the same direction as produced by the signal 56. Such short circuiting current is a supplement to application of a negative DC signal 56.

It is anticipated that solid state circuitry will be used, such that the entire applicator including reservoir, electrodes and electrical elements, including a power source for operation thereof, are effected in a small unitary device.

Figure 3:
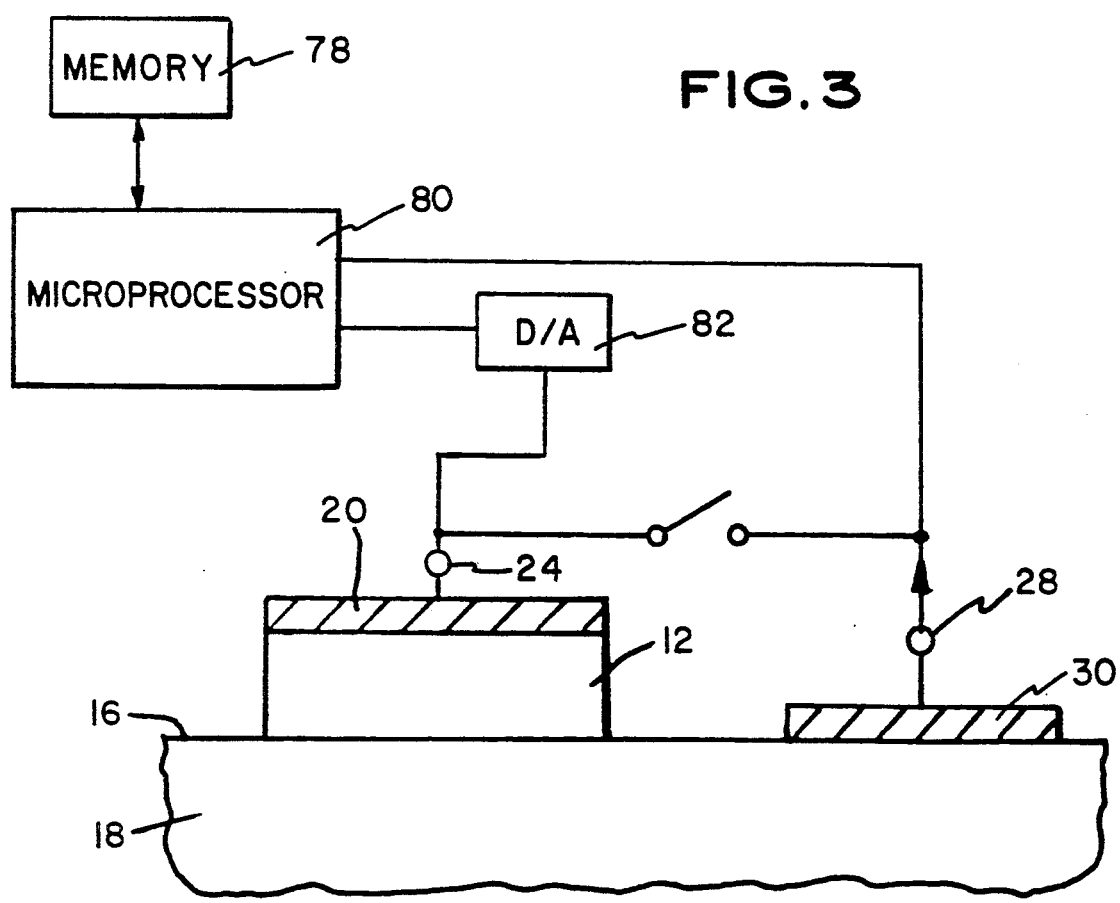
FIG. 3 is a schematic diagram of an alternative drug delivery applicator in accordance with the invention.

In the drug applicator in accordance with the invention of FIGS. 1 and 2, each signal is generated by an independent signal generating circuit. It should be understood that after the desired signals for a particular drug are selected, and special "tuning" is required for many drugs and combinations thereof, it may be possible to eliminate the individual signal generating circuits and replace such an arrangement with digital signals stored in a memory 78 (FIG. 3). The signals are read out in proper sequence under control of a microprocessor 80 and transformed by a digital to analog converter 82 to analog signals which are applied to the external terminals 24, 28. The total waveform, for example of FIG. 2a, is produced without need to have the actual circuits for signal generation in the drug applicator. On the other hand, for experimental work in adapting drugs for use in electrical transdermal applicators, it is advantageous to work "on-site" by superposing the signals from independent generating circuits in desired sequences and repetition rates, etc. until optimum performance characteristics are obtained in drug delivery. Combinations of stored and generated signals may also be utilized.

Figure 4:
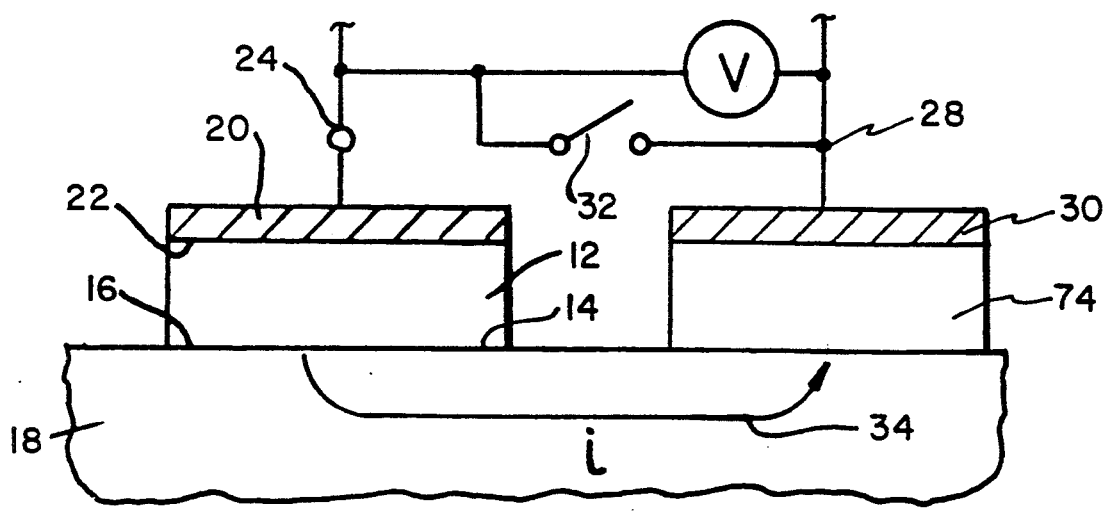
FIG. 4 is a partial schematic diagram of another alternative drug delivery applicator in accordance with the invention.

It should be understood that several drugs may be contained in the same reservoir and be delivered simultaneously. However, where one drug is delivered by one polarity of voltage and another drug is delivered by the opposite polarity, both drugs may be delivered in a single drug applicator in accordance with the invention by means of two reservoirs as illustrated in FIG. 4. Aside from addition of a second reservoir 74 in association with the electrode 30, the circuitry and concepts remain the same as in FIG. 1. The drug in the reservoir 12 is delivered to the skin 18 when the electrode 20 is positive relative to the skin and electrode 30 while at the same time, the drug in the reservoir 74 is delivered to the skin 18 because electrode 30 is negative with respect to the skin and the electrode 20.

Figure 5:
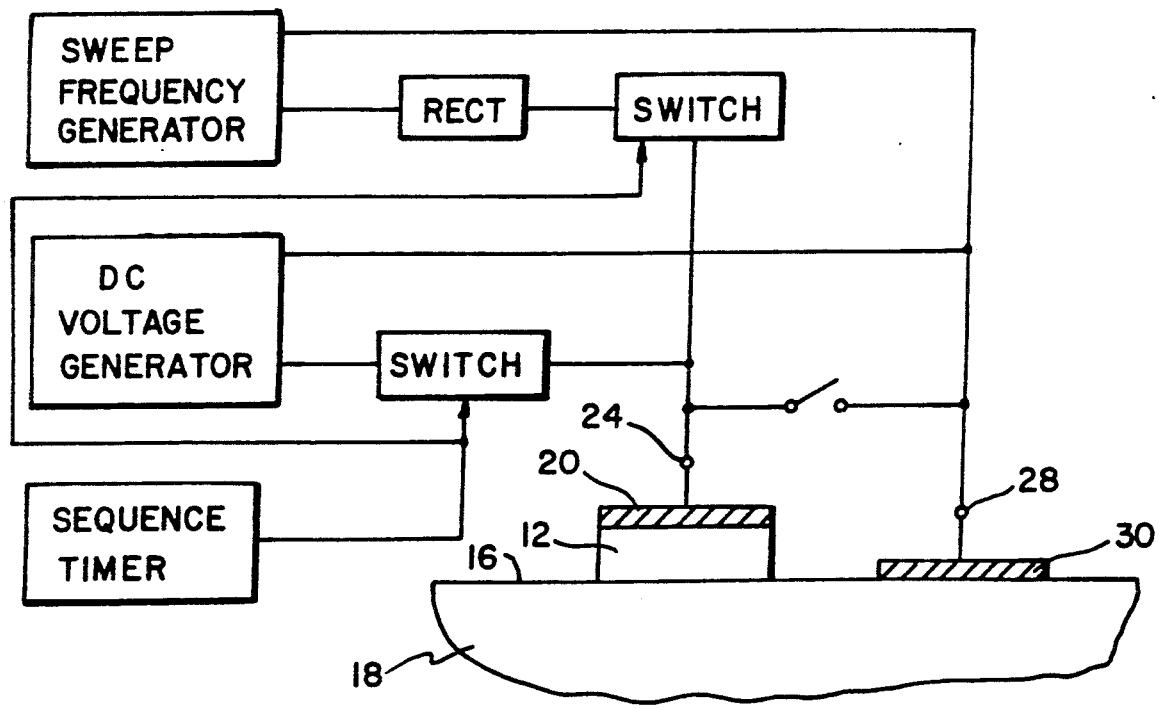
FIG. 5 is a schematic diagram of an alternative drug delivery applicator in accordance with the invention.

An alternative embodiment of a multi-signal electrical transdermal drug applicator in accordance with the invention is illustrated in FIG. 5. Electrodes 20, 30 and reservoir 12 are as described above.

However, the electrodes are driven alternately by rectified AC signals and the negative 0.8 volt signal. The 0.8 volt signal initiates the cycle, provides a preconditioning for the skin, as discussed hereinafter, and is applied for an interval C, e.g. a one minute interval. Then a rectified AC signal is applied across the terminals 24, 28 in a sweep of frequencies ranging from 10 Hz to 200 KHz. The sweep of the frequency range may be continuous or may be in steps as would be provided by a high frequency oscillator and a string of subsequent frequency divider stages (not shown), as is commonly known in electronic timekeeping. Different frequencies are selected for output by tapping the output of different stages in the divider network. The time devoted to each frequency may be selectively varied, and signal amplitude may be adjusted at different frequencies. In an embodiment in accordance with the invention, the frequency spectrum is swept in a range of 12 to 100 times per second, for a one minute period after which the negative 0.8 volt DC signal is applied, for example, for one minute, and so on. In this way, all frequencies of significance in enhancing drug delivery from the applicator 10 are applied along with harmonics which may be generated of those frequencies.

With regard to the circuit of FIG. 1 and the signals of FIG. 2, in an alternative embodiment in accordance with the invention, the rectified AC signal within the pulse 48 may be varied from pulse 48 to pulse 48. If there are 4800 repetitions (for example) of pulse 48 per minute, each such pulse represents an opportunity to apply a different selected frequency. Also, within the pulses 48 a band of frequencies may be swept as discussed above. Each pulse 48 may include an entire spectrum, for example from 10 Hz to 200 KHz and harmonics thereof or the full spectrum may be divided among a sequence of pulses 48.

Also, with regard to FIG. 2, it should be understood that different signals 48, 62, 68 may occur in any order and may in fact occur simultaneously, that is, with some degree of superposition of one signal with the other. Further, the signal 56 in addition to being applied for one interval C while the other signals 48, 62, 68 are absent, may be applied concurrently with all or any of the signals 48, 62, 68.

It should also be understood that within the pulse 48, the carrier frequency can be derived from sinusoidal or rectangular waveforms. The rectangular waveforms can have an unequal duty cycle which provides a two-frequency effect. FIG. 2a indicates a square wave carrier in pulse 48 with a ON/OFF ratio of ¼. A low duty cycle reduces power consumption and also lessens the possibility of skin damage. As stated above, the envelope for pulse 48 can be the half sine wave shape as illustrated or a rectangular waveform, or others.

Natural oscillatory phenomena exist in biological systems. By supplying energy above a critical rate, the various oscillatory units collapse into the lowest energy state and produce a strong, coherent single mode of oscillation which is a very efficient mechanism of targeted energy delivery.

At optimal frequencies the bio-piezoelectric semiconductors, such as enzymes, amplify the lattice vibrations by lowering the energy barriers. Low frequencies increase the penetration depth of the electrical field, thus increasing the rate of drug delivery when so applied. Low frequencies provide transport of energy over large molecular distances.

The cellular membranes alternately swell and contract, pumping in and out the transferred drug molecules under the influence of a varying electrical field.

Permittivity reflects the extent to which localized charge distribution can be distorted or polarized by an electrical field. Permittivity is associated with electrical double layers at membrane surfaces, solvated macromolecules and with polar molecules. At low frequency, polarization effect is fully realized. The fall in the relative permittivity at higher frequency due to rotational motion of protein molecules contributes fully to the polarizability of the solutions.

Dielectric dispersion depends on the effective mobility of ions on macromolecular surfaces.

At low frequencies the cell interior is shielded from the electrical field.

All collagenous tissues (skin) are piezoelectric.

Skin relaxation processes observed at 80 Hz and 2K-3KHZ are associated with the relaxation of counterions and with the "ice-like" water bound to skin proteins.

Alternating current changes the ionic concentrations in the cellular double-layers and cellular channels; these phenomena are frequency specific. For example, known frequency selective cellular ionic channels are 300 Hz for K ions, 200 Hz for Na channels, 11 Hz and 16 Hz for Ca ions.

Specific frequencies cause the stimulation of specific enzymes which can result in enhanced specific transport of certain active compounds through cellular layers. Concentration differentials of drugs across cellular membranes are frequency dependent. Rectangular waveforms provide a greater selectivity of the cellular adsorption process. The repetition rate of waveforms and amount of the superimposed DC determines the degree of kinetic coupling of the electrochemical surface events. Repetition rates in the range of 2-60 Hz appear to be less critical than higher frequencies.

A burst waveform, that is, an amplitude modulated square wave having a duty cycle which is less than 1 (ON/OFF) causes the cellular double layer to see an effectively wider pulse. Lower duty cycle pulses are less drug specific.

A 160 KHZ carrier frequency modifies the permeability to drugs of cellular membranes, and also acts as a vasodilator. This carrier also enhances electroosmosis.

Some frequencies effective with particular drug formulations are as follows: 140 KHz - oil suspensions; 100 KHz - colloidal suspensions; 80 KHz - water solutions; and 10 Hz - dispersions.

Low relaxation frequencies are found by permittivity measurements; conductivity data reflects high frequency phenomena.

Very low frequencies ($10^{-2}$ Hz) are related to hopping electron mechanisms and piezo relaxation. The side chains of bio-molecules cause relaxation effects at low frequency and retardational effects at higher frequencies (100 Hz) in the piezoelectric relaxation response.

Frequencies in the range of 0.025 Hz-10 Hz are also natural voltage fluctuations associated with active cellular transport, which the subject invention synchronizes and enhances.

Electrochemically switched activation and deactivation of ligands is a mechanism of transport of drug cations across waterimmiscible biological membranes. The ligand complexing and release are induced by a pulsating electrical current.

Hydroxylic compounds form molecular complexes via hydrogen bonds resulting in an increase in their dipole moment value.

For amino acids, the dipole concentration is maximum near the isoelectric point which is optimum for pulsating current stimulated electroosmotic drug delivery but not for the iontophoretic mode because dissolved ions increase the relaxation frequency. It is therefore desirable to minimize free ion concentration.

Water bound to biomacromolecular systems has an "ice-like" structure. It is advantageous to excite the system at the peaks associated with the maximum dielectric loss spectrum for ice, that is, between $10'Hz$ and $10^4$ Hz, depending on the hydrated particle radius. When water is bound to a collagen, the electret behavior of bound water produces relaxation time of about $10^{-5}$ sec.

Large Maxwell-Wagner dispersions exist at low frequencies such as $7\times10^{-3}$ Hz. The Maxwell-Wagner polarization effect causes the appearance of accumulated dielectric boundary charges and ionic migration. A pulsating field makes and breaks the molecular complexes of molecules having a permanent dipole and between nonpolar molecules polarized by inductions. The loose coupling between the donor and acceptor molecules produces a spread of adsorption frequencies. This effect, coupled with the effects of a D.C. field, allows for efficient transdermal drug delivery of compounds, especially the compounds which bind to body tissues.

Complex waveforms with power level distribution within given amplitude and frequency bands, as might be determined by Fourier series analysis, provide similar enhancement as the series elements for a given drug being delivered transdermally. This provides a circuit designer the option of minimizing waveform complexity and still obtaining the same effects.

The amplitude modulation signal is more important than the carrier frequency in the pulse 48 of FIG. 2a. This makes it possible, after choosing the modulation signal (envelope) to choose a carrier frequency which in itself has a desirable effect. In signal 48, FIG. 2a, the shown carrier signal has a frequency of approximately 2500 Hz, chosen to stimulate responses indicated above, with a ON/OFF duty cycle less than one. At the same time the envelope represents a third, much lower frequency of particular interest. The simultaneous use of different frequencies with low duty cycle can have a synergistic effect in addition to being energy efficient.

Reversing the electrical field is very important for transdermal drug delivery also because it induces "reptation" (long molecular strands snake their way through pores with molecules following the same path in "single file") of large molecular complexes; their mobility becomes independent of size.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings, shall be interpreted as illustrative and not in a limiting sense.

It is also to be understood that the following claims are intended to cover all the generic and specific features of the invention herein described, and all statements of the scope of the invention which, as a matter of language, might be said to fall therebetween.

What we claim is:

1. A transdermal applicator for delivering at least one drug through the skin to the blood circulation system of a patient over an extended period of time comprising:
   a drug reservoir for containing at least one drug and having means for attachment to the skin of a patient and making an electrical connection therewith at an interface between the reservoir and the skin of the patient,
   means connected to said reservoir including a source of variable electrical potential for effecting delivery of said drug transdermally into the blood of the patient when the applicator is in use, said source having one electrical terminal electrically connected to said reservoir spaced from said interface and a second terminal positionable on the surface of the skin of the patient spaced from said interface and in circuit with said interface when said applicator is in use, means in said source of variable electrical potential for cyclically generating a complex composite pulse signal applied to said one terminal, said reservoir and through said interface when said second terminal is in electrical contact with the skin of the patient, said complex composite pulse signal comprising a conditioning negative direct-current leading pulse followed by a sequence of pulses direct current pulses of different waveforms, amplitudes, frequencies and repetition rates, and timing means for applying the complex composite pulse signal as a composite total waveform signal with selected sequences of different time intervals of waveform components effective to develop and maintain current flow including current flow within blood capillaries of the patient in the same direction of current flow as the leading direct current pulse of the complex composite pulse signal.

2. A transdermal applicator for delivering at least one drug through the skin to the blood circulation system of a patient over an extended period of time according to claim 1, in which said timing means comprises spectral timing means comprising a timer and a microprocessor for selectively varying the time intervals of said sequence.

3. A transdermal applicator for delivering at least one drug through the skin to the blood circulation system of a patient over an extended period of time according to claim 1, in which said source of variable electrical potential comprises means for alternating the polarity of the source.

4. A transdermal applicator for delivering at least one drug through the skin to the blood circulation system of a patient over an extended period according to claim 1, including means for creating a short-circuit between said one terminal and said second terminal.

5. A transdermal applicator for delivering at least one drug through the skin to the blood circulation system of a patient over an extended period according to claim 1, including means for selectively interrupting pulse components of said complex signal in said sequences.

* * * * *